(12) United States Patent
Hipskind et al.

(10) Patent No.: US 9,000,023 B2
(45) Date of Patent: Apr. 7, 2015

(54) DISUBSTITUTED PHTHALAZINE HEDGEHOG PATHWAY ANTAGONISTS

(75) Inventors: Philip Arthur Hipskind, New Palastine, IN (US); Bharvin Kumar Patel, Westfield, IN (US); Takako Wilson (nee Takakuwa), Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 149 days.

(21) Appl. No.: 13/590,481

(22) Filed: Aug. 21, 2012

(65) Prior Publication Data

US 2012/0316174 A1 Dec. 13, 2012

Related U.S. Application Data

(62) Division of application No. 12/815,439, filed on Jun. 15, 2010, now Pat. No. 8,273,742.

(60) Provisional application No. 61/218,628, filed on Jun. 19, 2009.

(51) Int. Cl.
*A61K 31/415* (2006.01)
*C07D 231/12* (2006.01)
*C07D 401/14* (2006.01)

(52) U.S. Cl.
CPC .................................. *C07D 401/14* (2013.01)

(58) Field of Classification Search
USPC ........................................................ 514/248
See application file for complete search history.

(56) References Cited

U.S. PATENT DOCUMENTS

| | | | |
|---|---|---|---|
| 4,289,772 A | 9/1981 | Campbell et al. | |
| 7,981,892 B2 | 7/2011 | Hipskind et al. | |
| 2010/0324048 A1 | 12/2010 | Hipskind | |
| 2011/0301162 A1 | 12/2011 | Deak | |

FOREIGN PATENT DOCUMENTS

| | | |
|---|---|---|
| WO | WO9726258 A1 | 7/1997 |
| WO | WO 99/52534 A1 | 10/1999 |
| WO | WO 00/74706 A1 | 12/2000 |
| WO | WO03/088970 A2 | 10/2003 |
| WO | WO2005033288 A2 | 4/2005 |
| WO | WO 2005/080378 A1 | 9/2005 |
| WO | WO 2006/004589 A2 | 1/2006 |
| WO | WO 2006/028958 A1 | 4/2006 |
| WO | WO 2004/020599 A2 | 12/2006 |
| WO | WO 2008/028689 A1 | 3/2008 |
| WO | WO2008/110611 A1 | 9/2008 |
| WO | WO2008110611 A1 | 9/2008 |
| WO | WO2009/002469 A1 | 12/2008 |
| WO | WO2009002469 A1 | 12/2008 |
| WO | WO 2009/035568 A1 | 3/2009 |
| WO | WO2009134574 A2 | 11/2009 |
| WO | WO2010007120 A1 | 1/2010 |
| WO | WO 2010/056588 A1 | 5/2010 |
| WO | WO 2010/056620 A1 | 5/2010 |
| WO | WO 2010/062507 A1 | 6/2010 |
| WO | WO 2010/147917 A1 | 12/2010 |

OTHER PUBLICATIONS

Lear, N Engl J Med 366;23, Jun. 7, 2012.*
Yang, et al., Pathol. Oncol. Res. (2011) 17:387-391.*
Rudin, et al., N Engl J Med 361;12, Sep. 17, 2009.*
Hidalgo, et al., N Engl J Med 361;21, Nov. 19, 2009.*
Wikipedia, HEK 293 cells, http://en.wikipedia.org/wiki/HEK_293_cells, last modified on Jun. 3, 2014 and downloaded on Jul. 15, 2014.*
Pinedo, et al., "Translational Research: The Role of VEGF in Tumor Angiogenesis," The Oncologist, 5(suppl 1):1-2 (2000) [www.TheOncologist.com].
Patel, Bharvin, "Identification and Characterization of a Novel Smoothened Antagonist for the Treatment of Cancer with Deregulated Hedgehog Signaling"/Powerpoint Presentation, AACR 102nd Annual Meeting. Orlando, FL, 2011.
Bendall, Johanna et al., "A Phase I Dose-Escalation, Pharmacokinetic (PK) and Pharmacodynamic (PD) Evaluation of LY2940680, an Oral Smoothened (Smo) Inhibitor"/Poster, 24th European Cancer Organization (ECCO) EORTC-NCI-AACR Symposium on Molecular Targets and Cancer Therapeutics. Dublin, Ireland, 2012.
Frank-Kamenetsky, M., et al., "Small-molecular modulators of Hedgehog signaling: identification and characterization of Smoothened agonists and antagonists," Journal of Biolology vol. 1, Issue 2, Article 10, pp. 10.1-10.19 (2002).
Lee, J., et al., "A small-moleclar antagonist of the Hedgehog signaling pathway," ChemBioChem, vol. 8, pp. 1916-1919 (2007).
McMahon, G., VEGF Receptor Signaling in Tumor Angiogenisis. The Oncologist, 5(suppl 1):3-10 (2000). [www.TheOncologist.com].
Pinedo, et al., "Translational Research . . . ," The Oncologist, 5(suppl 1):1-2 [www.TheOncologist.com], (2000).
Tremblay, M., et al., "Semisynthetic cyclopamine analogues as potent and orally bioavailable Hedgehog pathway antagonists," J. Med. Chem., vol. 51, pp. 6646-6649 (2008).
Tremblay, M., et al., "Recent patents for Hedgehog pathway inhibitors for the treatment of malignancy," Expert Opin. Ther. Patents 19(8):1039-1056 (2009).

\* cited by examiner

*Primary Examiner* — Jeffrey H Murray
*Assistant Examiner* — Oluwafemi Masha
(74) *Attorney, Agent, or Firm* — Danica Hostettler

(57) ABSTRACT

The present invention provides novel 1,4-disubstituted phthalazine hedgehog pathway antagonists useful in the treatment of cancer.

6 Claims, No Drawings

DISUBSTITUTED PHTHALAZINE HEDGEHOG PATHWAY ANTAGONISTS

This application is a divisional of U.S. patent application Ser. No. 12/815,439 filed Jun. 15, 2010, which claims the priority of U.S. Provisional Application No. 61/218,628 filed Jun. 19, 2009.

The present invention relates to Hedgehog pathway antagonists and, more specifically, to novel 1,4-disubstituted phthalazines and therapeutic use thereof. The Hedgehog (Hh) signaling pathway plays an important role in embryonic pattern formation and adult tissue maintenance by directing cell differentiation and proliferation. The Hedgehog (Hh) protein family, which includes Sonic Hedgehog (Shh), Indian Hedgehog (Ihh), and Desert Hedgehog (Dhh) are secreted glycoproteins that undergo post-translational modifications, including autocatalytic cleavage and coupling of cholesterol to the amino-terminal peptide to form the fragment that possesses signaling activity. Hh binds to the twelve-pass transmembrane protein Ptch (Ptch1 and Ptch2), thereby alleviating Ptch-mediated suppression of Smoothened (Smo). Smo activation triggers a series of intracellular events culminating in the stabilization of the Gli transcription factors (Gli1, Gli2, and Gli3) and the expression of Gli-dependent genes that are responsible for cell proliferation, cell survival, angiogenesis and invasion.

Hh signaling has recently attracted considerable interest based on the discovery that aberrant activation of Shh signaling leads to the formation of various tumors, e.g., pancreatic cancer, medulloblastoma, basal cell carcinoma, small cell lung cancer, and prostate cancer. WO2005033288 discloses certain 1,4-disubstituted phthalazine compounds asserted to be hedgehog antagonists. Similarly, WO2008110611 discloses certain 1,4-disubstituted phthalazine compounds related to the diagnosis and treatment of pathologies related to the hedgehog pathway. WO2009002469 discloses certain 1,4-disubstituted phthalazine compounds that are asserted to be a treatment option for all tumors driven by inappropriate hedgehog signaling.

There still exists a need for potent hedgehog pathway inhibitors, particularly those having desirable toxicology profiles. The present invention provides novel 1,4-disubstituted phthalazines that are potent antagonists of this pathway. Particular compounds of the present invention provide desirable drug-drug interaction and related safety profiles with respect to reversible and/or mechanism-based irreversible CYP3A4 inhibition potential.

The present invention provides a compound of Formula I

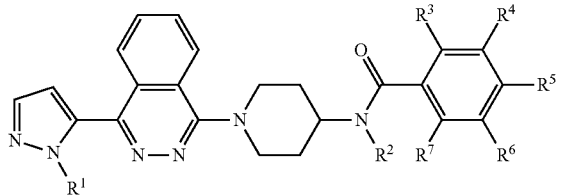

Formula I wherein, $R^1$ is hydrogen or methyl; $R^2$ is hydrogen or methyl; $R^3$, $R^4$, $R^5$, $R^6$, or $R^7$ are independently hydrogen, fluoro, chloro, cyano, trifluoromethyl, trifluoromethoxy, difluoromethoxy, methylsulfonyl, or trifluoromethylsulfonyl, provided that at least three of $R^3$, $R^4$, $R^5$, $R^6$ and $R^7$ are hydrogen; or a pharmaceutically acceptable salt thereof.

The present invention also provides a pharmaceutical composition comprising a compound of Formula I, or a pharmaceutically acceptable salt thereof, in combination with a pharmaceutically acceptable excipient, carrier or diluent.

The present invention also provides a method of treating cancer selected from the group consisting of brain cancer, basal cell carcinoma, esophagus cancer, stomach cancer, gastric cancer, pancreatic cancer, biliary tract cancer, prostate cancer, breast cancer, small-cell lung cancer, non-small cell lung cancer, B-cell lymphoma, multiple myeloma, ovarian cancer, colorectal cancer, liver cancer, kidney cancer, melanoma, head and neck cancer, mesothelioma, soft tissue sarcomas, bone sarcomas, leukemia, and testicular cancer in a mammal comprising administering to the mammal an effective amount of a compound of Formula I, or a pharmaceutically acceptable salt thereof.

Additionally, this invention provides a compound of Formula I, or a pharmaceutically acceptable salt thereof, for use in therapy. Also, this invention provides a compound of Formula I, or a pharmaceutically acceptable salt thereof, for use in the treatment of cancer. In particular, the cancer is selected from the group consisting of brain cancer, basal cell carcinoma, esophagus cancer, stomach cancer, gastric cancer, pancreatic cancer, biliary tract cancer, prostate cancer, breast cancer, small cell lung cancer, non-small cell lung cancer, B-cell lymphoma, multiple myeloma, ovarian cancer, colorectal cancer, liver cancer, kidney cancer, melanoma, head and neck cancer, mesothelioma, soft tissue sarcomas, bone sarcomas, leukemia, and testicular cancer.

This invention also provides use of a compound of Formula I, or a pharmaceutically acceptable salt thereof, in therapy. Additionally, this invention provides use of a compound of Formula I, or a pharmaceutically acceptable salt thereof, for the manufacture of a medicament for treating cancer. In particular, the cancer is selected from the group consisting of brain cancer, basal cell carcinoma, esophagus cancer, stomach cancer, gastric cancer, pancreatic cancer, biliary tract cancer, prostate cancer, breast cancer, small cell lung cancer, non-small cell lung cancer, B-cell lymphoma, multiple myeloma, ovarian cancer, colorectal cancer, liver cancer, kidney cancer, melanoma, head and neck cancer, mesothelioma, soft tissue sarcomas, bone sarcomas, leukemia, and testicular cancer.

Furthermore, this invention provides a pharmaceutical composition comprising a compound of Formula I, or a pharmaceutically acceptable salt thereof, as an active ingredient for treating cancer selected from the group consisting of brain cancer, basal cell carcinoma, esophagus cancer, stomach cancer, gastric cancer, pancreatic cancer, biliary tract cancer, prostate cancer, breast cancer, small cell lung cancer, non-small cell lung cancer, B-cell lymphoma, multiple myeloma, ovarian cancer, colorectal cancer, liver cancer, kidney cancer, melanoma, head and neck cancer, mesothelioma, soft tissue sarcomas, bone sarcomas, leukemia, and testicular cancer.

Particular compounds of Formula I, or a pharmaceutically acceptable salt thereof, are those wherein:
(a) $R^1$ is methyl;
(b) $R^2$ is methyl;
(c) $R^3$, $R^4$, $R^5$, $R^6$, or $R^7$ are independently hydrogen, fluoro, chloro, trifluoromethyl, or methylsulfonyl;
(d) $R^3$, $R^4$, $R^5$, $R^6$, or $R^7$ are independently hydrogen, fluoro, or trifluoromethyl;
(e) at least two of $R^3$, $R^4$, $R^5$, $R^6$ and $R^7$ are independently fluoro, chloro, trifluoromethyl, or methylsulfonyl, provided that $R^3$ and $R^7$ are not simultaneously hydrogen;

(f) at least two of $R^3$, $R^4$, $R^5$, $R^6$ and $R^7$ are independently fluoro or trifluoromethyl, provided that $R^3$ and $R^7$ are not simultaneously hydrogen;

(g) $R^4$, $R^6$ and $R^7$ are hydrogen;

(h) $R^3$ and $R^5$ are independently fluoro, chloro, trifluoromethyl, or methylsulfonyl; and $R^4$, $R^6$ and $R^7$ are hydrogen;

(i) $R^3$ and $R^5$ are independently fluoro or trifluoromethyl; and $R^4$, $R^6$ and $R^7$ are hydrogen;

(j) $R^1$ is methyl; and $R^2$ is methyl;

(k) $R^1$ is methyl; $R^2$ is methyl; and $R^3$, $R^4$, $R^5$, $R^6$, or $R^7$ are independently hydrogen, fluoro, chloro, trifluoromethyl, or methylsulfonyl;

(l) $R^1$ is methyl; $R^2$ is methyl; and $R^3$, $R^4$, $R^5$, $R^6$, or $R^7$ are independently hydrogen, fluoro, or trifluoromethyl;

(m) $R^1$ is methyl; $R^2$ is methyl; and at least two of $R^3$, $R^4$, $R^5$, $R^6$ and $R^7$ are independently fluoro, chloro, trifluoromethyl, or methylsulfonyl, provided that $R^3$ and $R^7$ are not simultaneously hydrogen;

(n) $R^1$ is methyl; $R^2$ is methyl; and at least two of $R^3$, $R^4$, $R^5$, $R^6$ and $R^7$ are independently fluoro or trifluoromethyl, provided that $R^3$ and $R^7$ are not simultaneously hydrogen;

(o) $R^1$ is methyl; $R^2$ is methyl; and $R^4$, $R^6$ and $R^7$ are hydrogen;

(p) $R^1$ is methyl; $R^2$ is methyl; $R^3$ and $R^5$ are independently fluoro, chloro, trifluoromethyl, or methylsulfonyl; and $R^4$, $R^6$ and $R^7$ are hydrogen; and (q) $R^1$ is methyl; $R^2$ is methyl; $R^3$ and $R^5$ are independently fluoro or trifluoromethyl; and $R^4$, $R^6$ and $R^7$ are hydrogen.

As used above, and throughout the description of the invention, the following terms, unless otherwise indicated, shall be understood to have the following meanings:

A "pharmaceutically acceptable carrier, diluent, or excipient" is a medium generally accepted in the art for the delivery of biologically active agents to mammals, e.g., humans.

"Pharmaceutically acceptable salts" refers to the relatively non-toxic, inorganic and organic salts of compounds of the present invention.

"Therapeutically effective amount" or "effective amount" means the amount of the compound of Formula I, or pharmaceutically acceptable salt thereof, of the present invention or pharmaceutical composition containing a compound of Formula I, or pharmaceutically acceptable salt thereof, of the present invention that will elicit the biological or medical response of or desired therapeutic effect on a tissue, system, animal, mammal or human that is being sought by the researcher, veterinarian, medical doctor or other clinician.

The terms "treatment," "treat," "treating," and the like, are meant to include slowing or reversing the progression of a disorder. These terms also include alleviating, ameliorating, attenuating, eliminating, or reducing one or more symptoms of a disorder or condition, even if the disorder or condition is not actually eliminated and even if progression of the disorder or condition is not itself slowed or reversed.

Under standard nomenclature used throughout this disclosure, the terminal portion of the designated side chain is described first, followed by the adjacent functionality toward the point of attachment. For example, a methylsulfonyl substituent is equivalent to $CH_3$—$SO_2$—.

The compounds of the present invention are capable of reaction, for example, with a number of inorganic and organic acids to form pharmaceutically acceptable acid addition salts. Such pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol 66, No. 1, January 1977.

The compounds of the present invention are preferably formulated as pharmaceutical compositions using a pharmaceutically acceptable carrier, diluent, or excipient and administered by a variety of routes. Preferably, such compositions are for oral or intravenous administration. Such pharmaceutical compositions and processes for preparing them are well known in the art. See, e.g., REMINGTON: THE SCIENCE AND PRACTICE OF PHARMACY (A. Gennaro, et al., eds., 19th ed., Mack Publishing Co., 1995).

The compound actually administered will be determined by a physician under the relevant circumstances, including the condition to be treated, the chosen route of administration, the actual compound or compounds administered, the age, weight, and response of the individual patient, and the severity of the patient's symptoms. Dosages per day normally fall within the range of about 0.1 to about 10 mg/kg of body weight. In some instances dosage levels below the lower limit of the aforesaid range may be more than adequate, while in other cases still larger doses may be employed.

The compounds of Formula I, or salts thereof, may be prepared by a variety of procedures known in the art, as well as those described in the Scheme, Preparations, and Examples below. The specific synthetic steps for each of the routes described may be combined in different ways to prepare compounds of Formula I, or pharmaceutically acceptable salts thereof.

The substituents, unless otherwise indicated, are as previously defined. The reagents and starting materials are generally readily available to one of ordinary skill in the art. Others may be made by standard techniques of organic and heterocyclic chemistry, techniques which are analogous to the syntheses of known structurally similar compounds, and the procedures described in the Preparations and Examples which follow including any novel procedures. The naming of the following Preparations and Examples is done using the Struct=Name naming feature in ChemDraw® Ultra 10.0.

As used herein, the following terms have the meanings indicated: "$Et_2O$" refers to diethyl ether; "DMF" refers to dimethylformamide; "DMSO" refers to dimethylsulfoxide; "DMAC" refers to N,N-dimethylacetamide; "NMP" refers to N-methylpyrrolidine; "MeOH" refers to methanol; "boc" or "t-boc" refers to tert-butoxycarbonyl; and "$IC_{50}$" refers to the concentration of an agent that produces 50% of the maximal inhibitory response possible for that agent.

Scheme

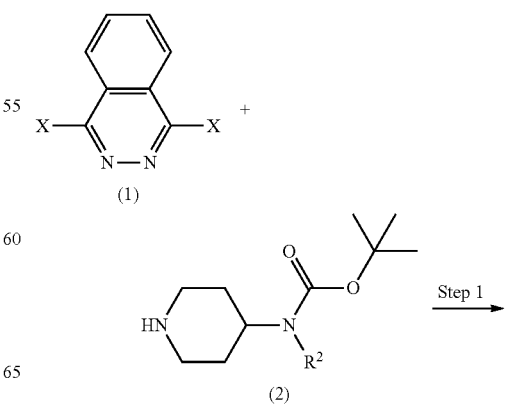

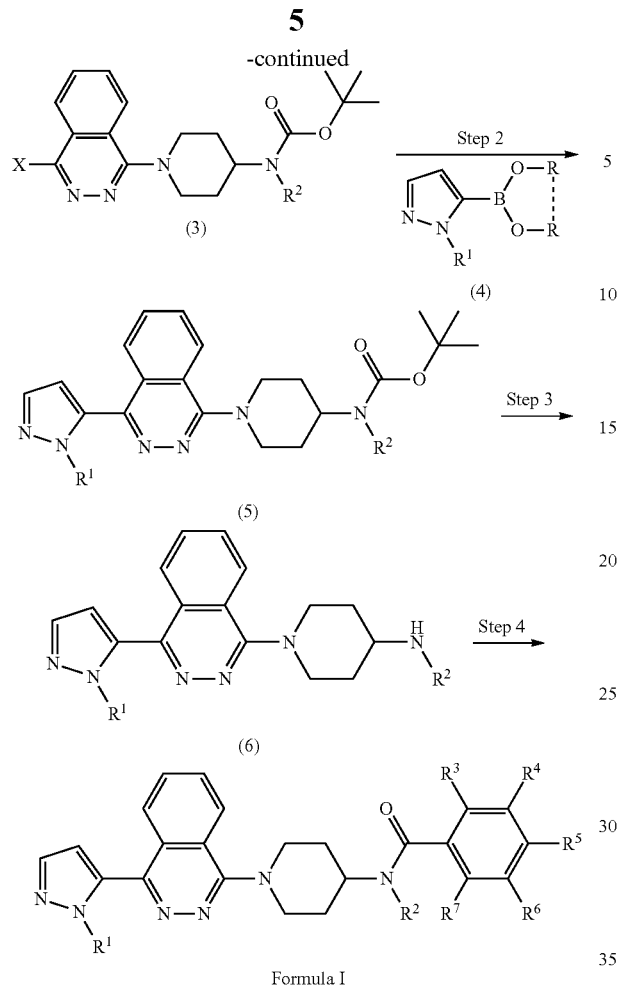

Formula I

A compound of Formula I can be prepared in accordance with reactions as depicted in the Scheme.

In Step 1, a dihalo substituted phthalazine (1) (X=Cl or Br) is reacted with a 4-amino boc protected piperidine (2) in a nucleophilic aromatic substitution (SNAr) to provide a halo piperidyl phthalazine of formula (3). The reaction proceeds in a dipolar aprotic solvent such as DMF, DMAC, or NMP, in the presence of an organic or inorganic base. Preferably, the reaction takes place in NMP, in the presence of potassium carbonate, at a temperature of 50-140° C.

In Step 2, a halo piperidyl phthalazine of formula (3) undergoes a Suzuki cross-coupling reaction with a pyrazole boronic ester or acid (4). For example, a halo piperidyl phthalazine (3) is combined with 1-methyl-1H-pyrazole-5-boronic acid pinacol ester in the presence of a palladium catalyst, such as tetrakis(triphenylphosphine)palladium and an inorganic base, such as sodium bicarbonate. The reaction proceeds in a solvent mixture of toluene/ethanol/water to give the pyrazolyl phthalazine of formula (5).

Step 3, is a simple boc deprotection accomplished under acidic conditions such as HCl in diethyl ether or dioxane to give the aminopiperidinyl phthalazine of formula (6). Methods for introducing and removing nitrogen and oxygen protecting groups are well known in the art (see, e.g., Greene and Wuts, *Protective Groups in Organic Synthesis*, 3$^{rd}$ Ed., John Wiley and Sons, New York, (1999)).

In Step 4, the aminopiperidinyl phthalazine of formula (6) is acylated to give the piperidinyl amide of Formula I. In one method, the amine is reacted with an appropriately substituted benzoyl chloride in an inert solvent, such as dichloromethane, in the presence of an organic base such as triethylamine or diisopropylethylamine. Alternatively, the amide is formed using an appropriately substituted benzoic acid. An active ester is formed using pentafluorophenyl diphenylphosphinate followed by reaction with the amine. The reaction proceeds in a solvent mixture of DMF/DMSO at a temperature of about −10 to 100° C. in the presence of an organic base, such as triethylamine or diisopropylethylamine Preparation 1 tert-Butyl 1-(4-chlorophthalazin-1-yl)piperidin-4-yl (methyl)carbamate

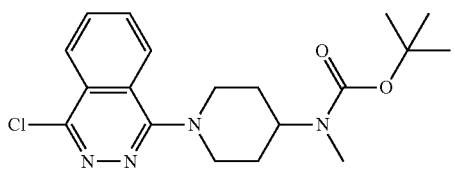

Heat a mixture of potassium carbonate (21.23 g, 153.6 mmol), 1,4-dichlorophthalazine (26 g, 128 mmol) and methyl-piperidin-4-yl carbamic acid tert-butyl ester (30.01 g, 134.4 mmol) in N-methylpyrrolidine (200 mL) at 80° C. overnight. Pour the reaction mixture into water, extract with dichloromethane, dry over Na$_2$SO$_4$, and concentrate under reduced pressure. Add diethylether and filter off the resulting solid (4-chlorophethalazin-1-ol from starting material impurity). Concentrate the filtrate. Purify the resulting residue by flash silica gel chromatography (hexane:ethyl acetate=2:1) to provide the title compound as a white solid (17.66 g, 37%). ES/MS m/z ($^{37}$Cl) 377.0 (M+1).

Preparation 2 tert-Butyl 1-(4-chlorophthalazin-1-yl)piperidin-4-ylcarbamate

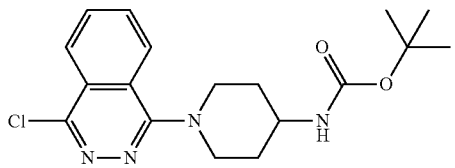 [SMILES: CC(C)(C)OC(=O)NC1CCN(c2nnc(Cl)c3ccccc23)CC1]

Prepare the title compound by essentially following the procedure described in Preparation 1, using piperidin-4-yl-carbamic acid tert-butyl ester. Cool the reaction mixture and pour into water (500 mL). Extract with ethyl acetate, wash with water, dry over Na$_2$SO$_4$, and remove the solvents under reduced pressure to provide the title compound as a yellow solid (36 g, 97%). ES/MS m/z 363.0 (M+1).

Preparation 3 tert-Butyl methyl(1-(4-(1-methyl-1H-pyrazol-5-yl)phthalazin-1-yl)piperidin-4-yl)carbamate

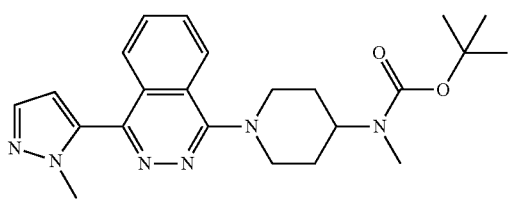 [SMILES: CN(C(=O)OC(C)(C)C)C1CCN(c2nnc(-c3ccnn3C)c3ccccc23)CC1]

Place sodium carbonate (3.82 g, 36.09 mmol), tert-butyl 1-(4-chlorophthalazin-1-yl) piperidin-4-yl(methyl)carbamate (6.8 g, 18.04 mmol) and 1-methyl-1H-pyrazole-5-boronic acid pinacol ester (5.63 g, 27.1 mmol) in a flask with a mixture of toluene (50 mL), ethanol (17 mL), and water (17 mL). Degas the mixture for 10 min with nitrogen gas. Add tetrakis(triphenylphosphine)palladium (0.4 g, 0.35 mmol) and heat the mixture at 74° C. overnight. Cool the mixture to ambient temperature and dilute with dichloromethane. Wash the organic portion with brine, dry over $Na_2SO_4$, and concentrate under reduced pressure. Purify the resulting residue by flash silica gel chromatography (hexane:ethyl acetate:2 M $NH_3$ in MeOH=20:5:1) to provide the title compound as a yellow foam (5.33 g, 70%). ES/MS m/z 423.2 (M+1).

Alternate procedure to prepare tert-butyl methyl(1-(4-(1-methyl-1H-pyrazol-5-yl)phthalazin-1-yl)piperidin-4-yl)carbamate: Preparations 4-6

Preparation 4

1,4-Dibromophthalazine

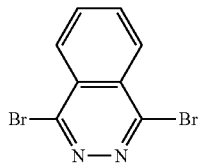

Charge a pressure tube with phosphorus pentabromide (24.5 g, 54.1 mmol) and 2,3-dihydro-phthalazine-1,4-dione (5.00 g, 30.8 mmol). Seal the tube and heat at 140° C. for 6-7 h. Allow to cool overnight. Carefully open the tube due to pressure. Chisel out the solid and pour into ice water. Allow to stir in ice water and collect the resulting solid by vacuum filtration. Dry in a vacuum oven to obtain the final product (8.31 g, 93%). ES/MS ($^{79}Br$, $^{81}Br$) m/z 288.8 (M+). Ref.: Can. J. Chem. 1965, 43, 2708.

Preparation 5 tert-Butyl 1-(4-bromophthalazin-1-yl)piperidin-4-yl(methyl)carbamate

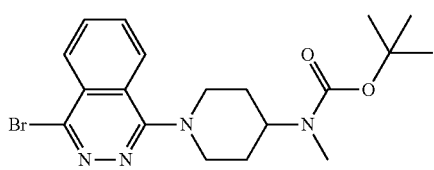

Combine 1,4-dibromophthalazine (0.70 g, 2.38 mmol), N-methylpyrrolidone (7.0 mL), potassium carbonate (395 mg, 2.86 mmol), and methyl-piperidin-4-yl-carbamic acid tert-butyl ester (532 mg, 2.38 mmol). Heat at 80° C. overnight. Cool and pour into water. Collect the solid and dry in a vacuum oven at ambient temperature overnight to obtain the final product (0.96 g, 95%). ES/MS m/z ($^{81}Br$) 421.0 (M+1).

Preparation 6 tert-Butyl methyl(1-(4-(1-methyl-1H-pyrazol-5-yl)phthalazin-1-yl)piperidin-4-yl)carbamate

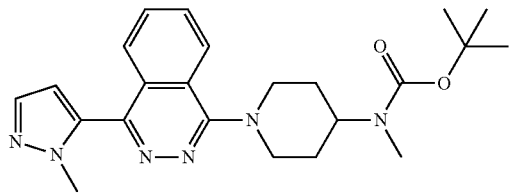 [SMILES: CN(C(=O)OC(C)(C)C)C1CCN(c2nnc(-c3ccnn3C)c3ccccc23)CC1]

Charge a reaction tube with tert-butyl 1-(4-bromophthalazin-1-yl)piperidin-4-yl(methyl)carbamate (500 mg, 1.2 mmol), 1-methyl-1H-pyrazole-5-boronic acid pinacol ester (370 mg, 1.8 mmol), sodium carbonate (252 mg, 2.4 mmol), toluene (3.75 mL), ethanol (1.25 mL), and water (1.25 mL). Degas the reaction mixture with nitrogen for 10 min. Add tetrakis(triphenylphosphine)palladium (137.1 mg, 118.7 µmol). Bubble nitrogen through the reaction mixture for another 10 min. Cap the reaction vial and heat at 90° C. overnight. Cool the reaction and filter through a silica gel pad eluting with 5% MeOH:$CH_2Cl_2$. Concentrate the fractions under reduced pressure. Purify the resulting residue using silica gel chromatography (2% 2 N $NH_3$ in MeOH:$CH_2Cl_2$) to obtain the final product (345.6 mg, 69%). ES/MS m/z 423.2 (M+1).

Preparation 7 tert-Butyl 1-(4-(1H-pyrazol-5-yl)phthalazin-1-yl)piperidin-4-yl(methyl)carbamate

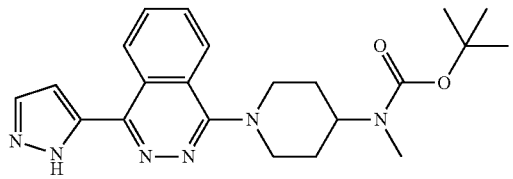 [SMILES: CN(C(=O)OC(C)(C)C)C1CCN(c2nnc(-c3ccn[nH]3)c3ccccc23)CC1]

Prepare the title compound by essentially following the procedure described in Preparation 3, using tert-butyl 1-(4-chlorophthalazin-1-yl)piperidin-4-yl(methyl)carbamate and 1H-pyrazole-3-boronic acid pinacol ester to provide 580 mg, (67%). ES/MS m/z 409.2 (M+1).

Preparation 8 tert-Butyl 1-(4-(1-methyl-1H-pyrazol-5-yl)phthalazin-1-yl)piperidin-4-ylcarbamate

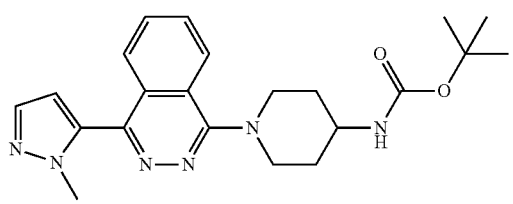 [SMILES: Cn1nccc1-c1nnc(N2CCC(NC(=O)OC(C)(C)C)CC2)c2ccccc12]

Prepare the title compound by essentially following the procedure described in Preparation 3, using tert-butyl 1-(4-chlorophthalazin-1-yl)piperidin-4-ylcarbamate to provide 5.92 g (94%). ES/MS m/z 308.8 (M+).

Preparation 9

N-methyl-1-(4-(1-methyl-1H-pyrazol-5-yl)phthalazin-1-yl)piperidin-4-amine

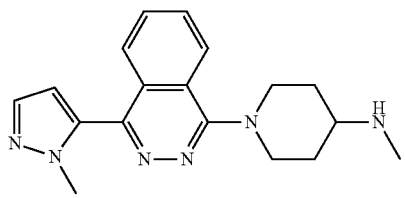 [SMILES: CNC1CCN(c2nnc(-c3ccnn3C)c3ccccc23)CC1]

Dissolve tert-butyl methyl(1-(4-(1-methyl-1H-pyrazol-5-yl)phthalazin-1-yl)piperidin-4-yl)carbamate (7.77 g, 18.39 mmol) in dichloromethane (100 mL). Add an excess of 1 M hydrogen chloride in diethyl ether (20 mL, 80 mmol) to the solution and stir at ambient temperature for 2 h. Concentrate under reduced pressure. Purify the resulting residue by flash silica gel chromatography (dichloromethane:2 M NH$_3$ in MeOH=10:1) to provide the title compound as a yellow foam (5.83 g, 98%). ES/MS m/z 323.2 (M+1).

Prepare the intermediates in the table below by essentially following the procedure described in Preparation 9, with the exception that the appropriate t-Boc protected amine is deprotected using 4 M HCl in dioxane.

| Prep. No. | Chemical name | Structure | ES/MS m/z |
|---|---|---|---|
| 10 | 1-(4-(1H-Pyrazol-5-yl)phthalazin-1-yl)-N-methyl-piperidin-4-amine | 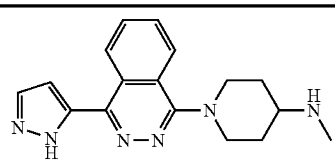 | 309.2 (M+) |
| 11 | 1-(4-(1-Methyl-1H-pyrazol-5-yl)phthalazin-1-yl)piperidin-4-amine | 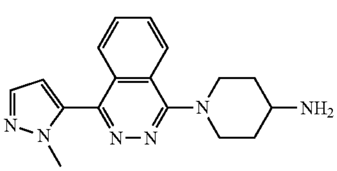 [SMILES: Cn1nccc1-c1nnc(N2CCC(N)CC2)c2ccccc12] | 408.8 (M+) |

EXAMPLE 1

4-Fluoro-N-methyl-N-(1-(4-(1-methyl-1H-pyrazol-5-yl)phthalazin-1-yl)piperidin-4-yl)-2-(trifluoromethyl)benzamide

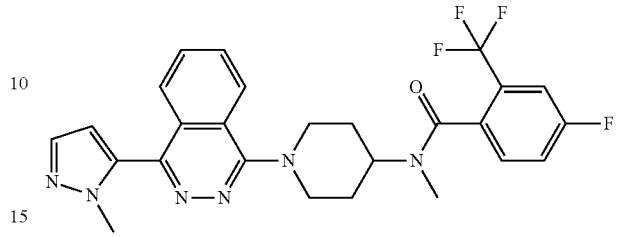

Treat a solution of N-methyl-1-(4-(1-methyl-1H-pyrazol-5-yl)phthalazin-1-yl)piperidin-4-amine (2.8 g, 8.68 mmol) and triethylamine (3.36 mL, 26.1 mmol) in CH$_2$Cl$_2$ (30 mL) with 4-fluoro-2-(trifluoromethyl)benzoyl chloride (2.14 mL, 10.42 mmol). Stir for 3 h at ambient temperature. Concentrate the reaction mixture under reduced pressure. Purify the resulting residue by flash silica gel chromatography (hexane:ethyl acetate:2 M NH$_3$ in MeOH=20:5:1) to provide the free base as a yellow foam (3.83 g, 86%). ES/MS m/z 513.0 (M+1).

EXAMPLE 1a

4-Fluoro-N-methyl-N-(1-(4-(1-methyl-1H-pyrazol-5-yl)phthalazin-1-yl)piperidin-4-yl)-2-(trifluoromethyl)benzamide hydrochloride Dissolve 4-fluoro-N-methyl-N-(1-(4-(1-methyl-1H-pyrazol-5-yl)phthalazin-1-yl)piperidin-4-yl)-2-(trifluoromethyl)benzamide (7.13 g, 13.91 mmol) in dichloromethane (100 mL) and add excess 1 N HCl in diethyl ether (30 mL, 30 mmol). Remove the solvents under reduced pressure to provide the title compound (7.05 g, 92%). ES/MS m/z 513.0 (M+1). NMR showed a 2:1 mixture of amide rotamers. Major rotamer; $^1$H NMR (400 MHz, DMSO-d$_6$): δ 8.34 (m, 1H), 8.26 (m, 2H), 7.95 (m, 1H), 7.75 (m, 1H), 7.64 (m, 2H), 7.55 (m, 1H), 6.72 (d, 1H, J=2 Hz), 5.15 (br, 1H), 4.71 (m, 1H), 4.22 (m, 2H), 3.84 (s, 3H), 3.48 (m, 2H), 2.65 (s, 3H), 2.19 (m, 2H), 1.89 (m, 2H). Minor rotamer; $^1$H NMR (400 MHz, DMSO-d$_6$): δ 8.27 (m, 1H), 8.24 (m, 2H), 7.94 (m, 1H), 7.73 (m, 1H), 7.63 (m, 3H), 6.70 (d, 1H, J=2 Hz), 5.15 (br, 1H), 4.71 (m, 1H), 4.07 (m, 2H), 3.81 (s, 3H), 3.16 (m, 2H), 2.92 (s, 3H), 1.90 (m, 2H), 1.62 (m 2H).

Prepare the amides in the table below by essentially following the procedures described in Example 1 and 1a, using the appropriate piperidinylphthalazine and substituted benzoyl chloride.

| Ex. No. | Chemical name | Structure | ES/MS m/z |
|---|---|---|---|
| 2 | 2-Fluoro-N-methyl-N-(1-(4-(1-methyl-1H-pyrazol-5-yl)phthalazin-1-yl)piperidin-4-yl)-3-(trfluoromethyl)benzamide hydrochloride | 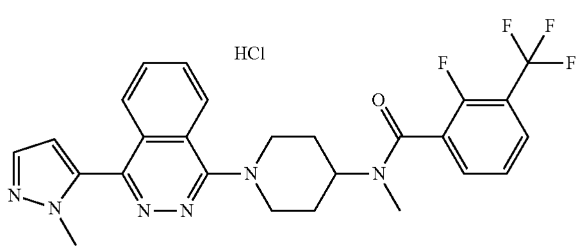 [SMILES: CN(C(=O)c1cccc(C(F)(F)F)c1F)C1CCN(c2nnc(-c3ccnn3C)c3ccccc23)CC1 ; Cl] | 513.0 (M + 1) |

-continued

| Ex. No. | Chemical name | Structure | ES/MS m/z |
|---|---|---|---|
| 3 | N-Methyl-N-(1-(4-(1-methyl-1H-pyrazol-5-yl)phthalazin-1-yl)piperidin-4-yl)-4-(trifluoromethoxy)benzamide hydrochloride | 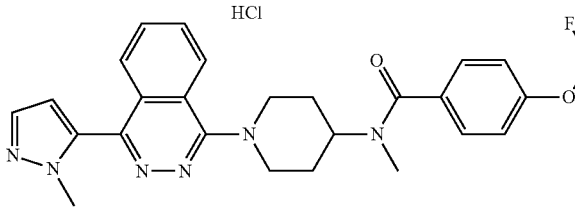 | 511.0 (M + 1) |
| 4 | N-Methyl-N-(1-(4-(1-methyl-1H-pyrazol-5-yl)phthalazin-1-yl)piperidin-4-yl)-2-(trifluoromethoxy)benzamide hydrochloride | 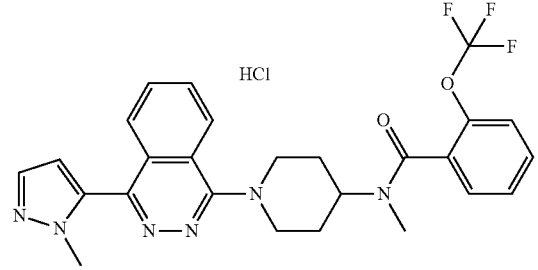 [SMILES: CN(C(=O)c1ccccc1OC(F)(F)F)C1CCN(c2nnc(-c3ccnn3C)c3ccccc23)CC1 ; Cl] | 511.0 (M + 1) |
| 5 | 5-Fluoro-N-methyl-N-(1-(4-(1-methyl-1H-pyrazol-5-yl)phthalazin-1-yl)piperidin-4-yl)-2-(trifluoromethyl)benzamide hydrochloride | 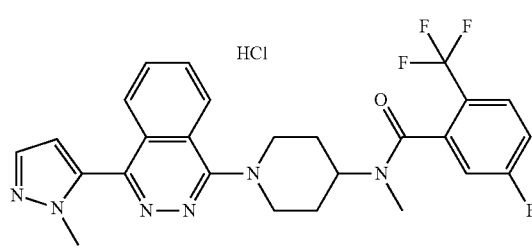 | 513.0 (M + 1) |
| 6 | 3,5-Dichloro-N-methyl-N-(1-(4-(1-methyl-1H-pyrazol-5-yl)phthalazin-1-yl)piperidin-4-yl)benzamide hydrochloride | 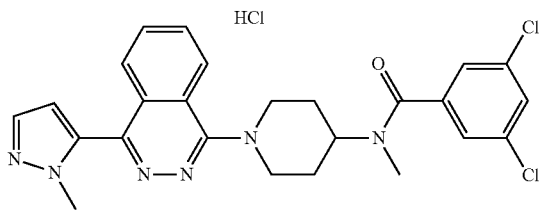 [SMILES: Cl ; CN(C(=O)c1cc(Cl)cc(Cl)c1)C1CCN(c2nnc(-c3ccnn3C)c3ccccc23)CC1] | ($^{35}$Cl) 495.0 (M + 1) |
| 7 | 4-Cyano-N-methyl-N-(1-(4-(1-methyl-1H-pyraozl-5-yl)phthalazin-1-yl)piperidin-4-yl)benzamide hydrochloride | 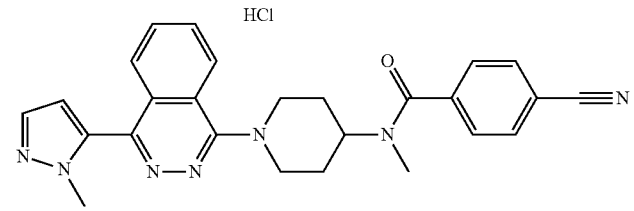 | 526.2 (M + 1) |
| 8 | N-(1-(4-(1H-Pyrazol-5-yl)phthalazin-1-yl)piperidin-4-yl)-4-fluoro-N-methyl-2-(trifluoromethyl)benzamide hydrochloride | 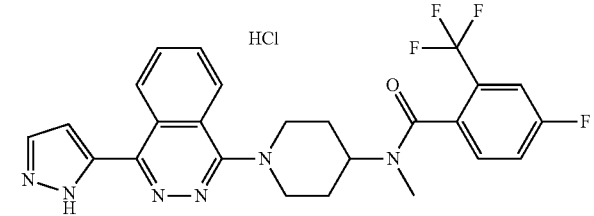 [SMILES: CN(C(=O)c1ccc(F)cc1C(F)(F)F)C1CCN(c2nnc(-c3ccn[nH]3)c3ccccc23)CC1 ; Cl] | 499.0 (M + 1) |

-continued

| Ex. No. | Chemical name | Structure | ES/MS m/z |
|---|---|---|---|
| 9 | N-(1-(4-(1-Methyl-1H-pyrazol-5-yl)phthalazin-1-yl)piperidin-4-yl)-4-(trifluoromethoxy)benzamide hydrochloride | 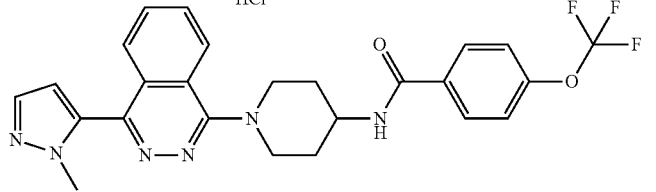 | 497.0 (M + 1) |
| 10 | N-(1-(4-(1-Methyl-1H-pyrazol-5-yl)phthalazin-1-yl)piperidin-4-yl)-2-(trifluoromethoxy)benzamide hydrochloride | 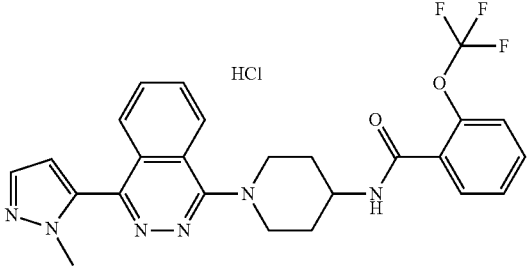 [SMILES: Cn1nccc1-c1nnc(N2CCC(NC(=O)c3ccccc3OC(F)(F)F)CC2)c2ccccc12 ; Cl] | 497.0 (M + 1) |
| 11 | 5-Fluoro-N-(1-(4-(1-methyl-1H-pyrazol-5-yl)phthalazin-1-yl)piperidin-4-yl)-2-(trifluoromethyl)benzamide hydrochloride | 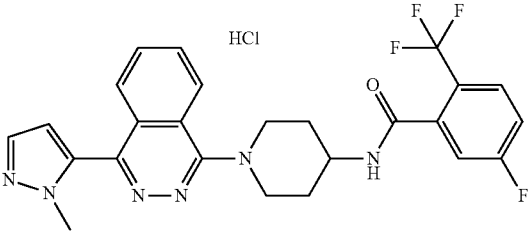 [SMILES: Cn1nccc1-c1nnc(N2CCC(NC(=O)c3cc(F)ccc3C(F)(F)F)CC2)c2ccccc12 ; Cl] | 499.0 (M + 1) |
| 12 | 4-Fluoro-N-(1-(4-(1-methyl-1H-pyrazol-5-yl)phthalazin-1-yl)piperidin-4-yl)-2-(trifluoromethyl)benzamide hydrochloride | 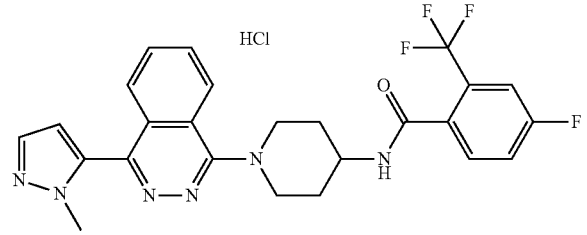 [SMILES: Cn1nccc1-c1nnc(N2CCC(NC(=O)c3ccc(F)cc3C(F)(F)F)CC2)c2ccccc12 ; Cl] | 499.0 (M + 1) |
| 13 | 4-Cyano-N-(1-(4-(1-methyl-1H-pyrazol-5-yl)phthalazin-1-yl)piperidin-4-yl)benzamide hydrochloride | 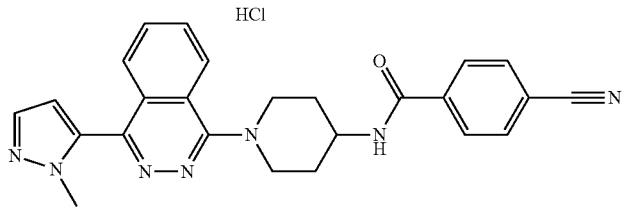 [SMILES: Cl ; Cn1nccc1-c1nnc(N2CCC(NC(=O)c3ccc(C#N)cc3)CC2)c2ccccc12] | 438.0 (M + 1) |

EXAMPLE 14

4-Chloro-N-methyl-N-(1-(4-(1-methyl-1H-pyrazol-5-yl)phthalazin-1-yl)piperidin-4-yl)-2-(methylsulfonyl)benzamide hydrochloride

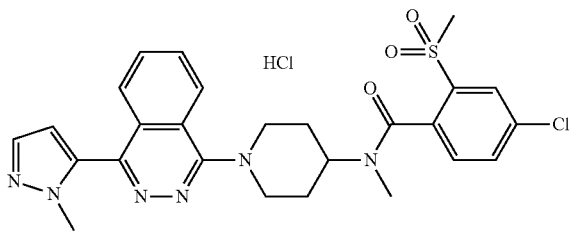 [SMILES: CN(C(=O)c1ccc(Cl)cc1S(C)(=O)=O)C1CCN(c2nnc(-c3ccnn3C)c3ccccc23)CC1 ; Cl]

Dissolve N-methyl-1-(4-(1-methyl-1H-pyrazol-5-yl)phthalazin-1-yl)piperidin-4-amine (100 mg, 0.31 mmol), 4-chloro-2-(methylsulfonyl)benzoic acid (87 mg, 0.37 mmol) and diisopropylethylamine (0.26 mL, 1.5 mmol) in DMF:DMSO=4:1 (2 mL) at 60° C. Cool to 0° C. and add pentafluorophenyl diphenylphosphinate (250 mg, 0.65 mmol) in DMF:DMSO=1:1 (1 mL) to the solution. Stir the mixture at 60° C. overnight. Cool the reaction mixture to ambient temperature and dilute with $CH_2Cl_2$, wash with brine, dry over $Na_2SO_4$, and concentrate under reduced pressure. Purify the resulting residue by flash silica gel chromatography (hexane:ethyl acetate:2 M $NH_3$ in MeOH=20:5:1) to provide the product. Add excess 1 N HCl in diethyl ether (1 mL, 10 mmol) to the isolated product and remove the solvent to provide the title compound (150 mg, 84%). ES/MS m/z 539.0 (M+1).

Prepare the amides in the table below by essentially following the procedure described in Example 14, using the appropriate piperidinylphthalazine and substituted benzoic acid.

| Ex. No. | Chemical name | Structure | ES/MS m/z |
|---|---|---|---|
| 15 | N-Methyl-N-(1-(4-(1-methyl-1H-pyrazol-5-yl)phthalazin-1-yl)piperidin-4-yl)-2-(methylsulfonyl)benzamide hydrochloride | 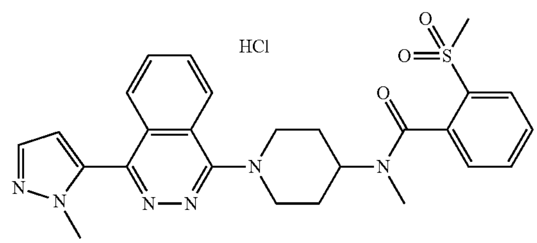 [SMILES: CN(C(=O)c1ccccc1S(C)(=O)=O)C1CCN(c2nnc(-c3ccnn3C)c3ccccc23)CC1 ; Cl] | 505.0 (M + 1) |
| 16 | 5-Fluoro-N-methyl-N-(1-(4-(1-methyl-1H-pyrazol-5-yl)phthalazin-1-yl)piperidin-4-yl)-2-(methylsulfonyl)benzamide hydrochloride | 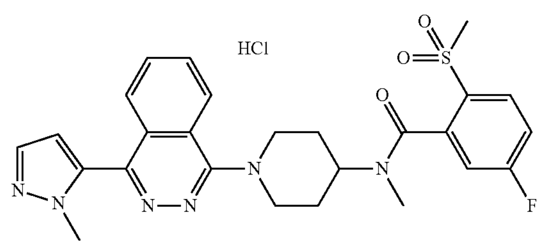 | 476.0 (M + 1) |
| 17 | N-Methyl-N-(1-(4-(1-methyl-1H-pyrazol-5-yl)phthalazin-1-yl)piperidin-4-yl)-2-(trifluoromethylsulfonyl)benzamide hydrochloride | 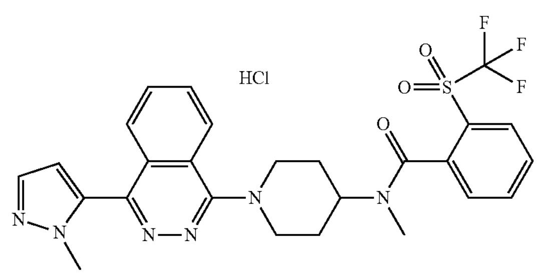 [SMILES: CN(C(=O)c1ccccc1S(=O)(=O)C(F)(F)F)C1CCN(c2nnc(-c3ccnn3C)c3ccccc23)CC1 ; Cl] | 559.0 (M + 1) |
| 18 | 2-Chloro-4-fluoro-N-methyl-N-(1-(4-(1-methyl-1H-pyrazol-5-yl)phthalazin-1-yl)piperidin-4-yl)benzamide hydrochloride | 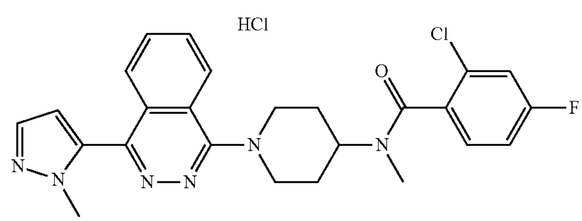 [SMILES: Cl ; CN(C(=O)c1ccc(F)cc1Cl)C1CCN(c2nnc(-c3ccnn3C)c3ccccc23)CC1] | ($^{35}$Cl) 479.0 (M + 1) |

-continued

| Ex. No. | Chemical name | Structure | ES/MS m/z |
|---|---|---|---|
| 19 | 2-Cyano-N-methyl-N-(1-(4-(1-methyl-1H-pyrazol-5-yl)phthalazin-1-yl)piperidin-4-yl)benzamide hydrochloride | 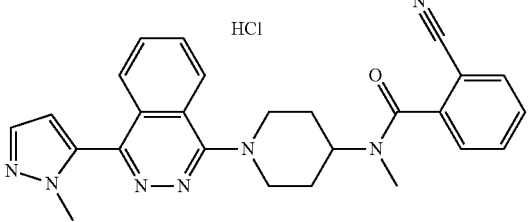 | 452.0 (M + 1) |
| 20 | 4-(Difluoromethoxy)-N-methyl-N-(1-(4-(1-methyl-1H-pyrazol-5-yl)phthalazin-1-yl)piperidin-4-yl)benzamide hydrochloride | 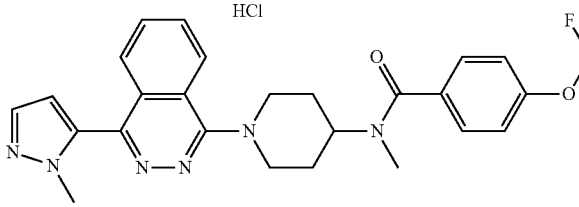 | 493.0 (M + 1) |
| 21 | N-(1-(4-(1-Methyl-1H-pyrazol-5-yl)phthalazin-1-yl)piperidin-4-yl)-2-(methylsulfonyl)benzamide hydrochloride | 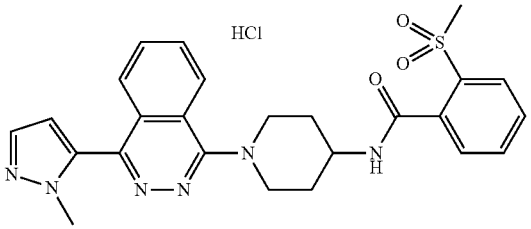 [SMILES: Cn1nccc1-c1nnc(N2CCC(NC(=O)c3ccccc3S(C)(=O)=O)CC2)c2ccccc12 ; Cl] | 491.0 (M + 1) |
| 22 | 4-Chloro-N-(1-(4-(1-methyl-1H-pyrazol-5-yl)phthalazin-1-yl)piperidin-4-yl)-2-(methylsulfonyl)benzamide hydrochloride | 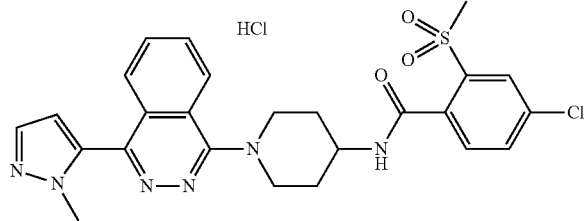 [SMILES: Cn1nccc1-c1nnc(N2CCC(NC(=O)c3ccc(Cl)cc3S(C)(=O)=O)CC2)c2ccccc12 ; Cl] | ($^{35}$Cl) 525.0 (M + 1) |
| 23 | N-(1-(4-(1-Methyl-1H-pyrazol-5-yl)phthalazin-1-yl)piperidin-4-yl)-2-(trifluoromethylsulfonyl)benzamide hydrochloride | 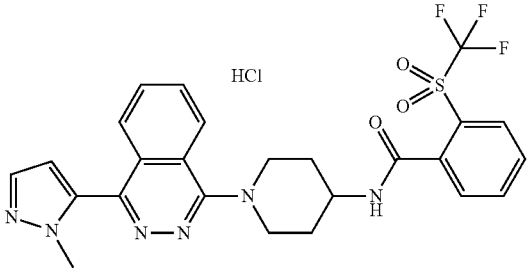 [SMILES: Cn1nccc1-c1nnc(N2CCC(NC(=O)c3ccccc3S(=O)(=O)C(F)(F)F)CC2)c2ccccc12 ; Cl] | 545.0 (M + 1) |
| 24 | 2-Chloro-4-fluoro-N-(1-(4-(1-methyl-1H-pyrazol-5-yl)phthalazin-1-yl)piperidin-4-yl)benzamide hydrochloride | 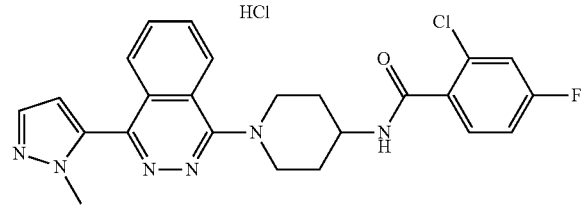 [SMILES: Cl ; Cn1nccc1-c1nnc(N2CCC(NC(=O)c3ccc(F)cc3Cl)CC2)c2ccccc12] | ($^{35}$Cl) 465.0 (M + 1) |

Hedgehog has been implicated as a survival factor for the following cancers: basal cell carcinoma; upper gastro intestinal tract cancers (esophagus, stomach, pancreas, and biliary tract); prostate cancer; breast cancer; small cell lung cancer; non-small cell lung cancer; B-cell lymphoma; multiple myeloma; gastric cancer; ovarian cancer; colorectal cancer; liver cancer; melanoma; head and neck cancer; mesothelioma; soft tissue sarcomas; bone sarcomas; leukemia; testicular cancer; kidney cancer; and brain cancer.

Elements of the hedgehog pathway have been asserted to be potential drug targets for the treatment of cancers. A Daoy cell line established from medulloblastoma tumor (ATCC, HTB-186), is responsive to Hh ligands. When these cells are treated with exogenously added Shh-conditioned media, Hh signaling pathway is activated and results in an increased expression of Gli1. Cyclopamine, an alkaloid isolated from the corn lily *Veratrum californicum* is a weak hedgehog antagonist and has been shown to suppress the expression of Gli1 in response to Shh stimulation. Recent observations suggest that cyclopamine inhibits the growth of cultured medulloblastoma cells and allografts. Using this Daoy cell model system, potent inhibitors of hedgehog signaling pathways can be identified. Since the compounds of the present invention are hedgehog antagonists, they are suitable for treating the aforementioned tumor types.

Determination of Biological Activity $IC_{50}$:
Functional Assay for Measuring the Inhibition of Gli1 in Daoy cells The following assay protocol and results thereof further demonstrate the utility and efficacy of the compounds and methods of the current invention. Functional assays provide support that the compounds of the present invention exhibit the ability to inhibit Shh signaling. All ligands, solvents, and reagents employed in the following assay are readily available from commercial sources or can be readily prepared by one skilled in the art.

Biological activity is determined using a functional assay in Daoy neuronal cancer cells and measures levels of Gli1 ribonucleic acid via a bDNA (branched deoxyribonucleic acid) assay system (Panomics, Inc., Fremont, Calif.). Gli was originally discovered in a Glioblastoma cell line and encodes a zinc finger protein that is activated by Shh signaling. The maximum response is obtained by inducing Gli1 transcription in the Daoy cells with conditioned medium (human embryonic kidney, HEK-293 cells stably expressing recombinant Shh) for 24 hours and then measuring the amount of stimulated Gli1 transcript. The minimum response is the amount of Gli1 transcript inhibited with a control compound in Daoy cells that have been stimulated with conditioned media (human embryonic kidney, HEK-293 cells stably expressing recombinant Shh) for 24 hours.

The bDNA assay system utilizes the technology of branched-chain DNA to allow amplification of a target ribonucleic acid (transcript). The technology employs three types of synthetic hybrid short Gli1-specific cDNA probes that determine the specificity of the target transcript [capture extenders (CEs), label extenders (LEs), and blockers (BLs)] that hybridize as a complex with the target transcripts to amplify the hybridization signal. The addition of a chemilumigenic substrate during the amplification step allows for detection using luminescence.

Daoy cells are grown to confluency in tissue culture T225-flasks in Daoy growth media containing Minimum Essential Medium (MEM) plus 10% Fetal Bovine Serum (FBS) with 0.1 nM non-essential amino acids and 1 mM sodium pyruvate. The cells are removed from the T225-flasks using trypsin ethylenediaminetetraacetic acid (EDTA), centrifuged, resuspended in media, and then counted.

The Daoy cells are then seeded at 50,000 cells per well in growth media in Costar 96 well clear tissue culture plates and allowed to incubate overnight at 37° C. under 5% carbon dioxide ($CO_2$). The cells are washed one time in phosphate buffered saline (PBS) followed by addition of 100 μL of Shh Conditioned Media (Shh-CM) to stimulate levels of Gli1 expression. Shh-CM is diluted to achieve maximum stimulation using control growth media—0.1% FBS/DMEM (Dulbeccos Modified Eagle Medium). Daoy cells treated with Shh-CM are then treated with various concentrations of hedgehog inhibitors ranging from approximately 1 μM to 0.1 nM. Test compounds are allowed to incubate for 24 hours at 37° C. under 5% $CO_2$.

The measurement of the Gli1 transcript is performed by using the Quantigene 2.0 Gli1 assay as described by the manufacturer (Panomics, Inc.). Prepare a diluted lysis mixture (DLM) buffer, which includes Proteinase K. After a 24 hour incubation with compound, the cells are washed one time with PBS and 180 μL of DLM is added to the cells. The cell plate containing the lysis buffer is sealed and placed at 55° C. for 30 to 45 minutes. The resulting cell lysates are then triturated 5 times. A working probe set containing Gli1 probes is made by diluting the probes in the DLM according to the manufacturer's directions, and then 20 μL of the working probe set is added to the bDNA assay plates along with 80 μL of the Daoy lysates. The plates are sealed and incubated overnight at 55° C. The bDNA plates are then processed according to the manufacturer's directions. The signal is quantified by reading the plates on a Perkin Elmer Envision reader detecting luminescence. The luminescent signal is directly proportional to the amount of target transcript present in the sample.

The luminescent signal data from the functional assay are used to calculate the $IC_{50}$ for the in vitro assay. The data are calculated based on the maximum control values (Daoy cells treated with Shh-CM) and the minimum control value (Daoy cells treated with Shh-CM and an inhibitory concentration of a control compound, 1 μM of N-(3-(1H-benzo[d]imidazol-2-yl)-4-chlorophenyl)-3,5-dimethoxybenzamide). A four parameter logistic curve fit is used to generate the $IC_{50}$ values using ActivityBase software programs version 5.3, equation 205 (*Assay Guidance Manual Version* 5.0, 2008, Eli Lilly and Company and NIH Chemical Genomics Center).

Following the protocol described, the compounds exemplified herein display an $IC_{50}$ of <40 nM. For example, the compound of Example 1a has an $IC_{50}$ of approximately 2.4 nM with a standard error of 0.5 (n=7, calculated as a geometric mean and geometric standard error) in the assay described above. These results provide evidence that the compounds of the present invention are potent hedgehog antagonists and, as such, are useful as anticancer agents.

CYP3A4 Inhibition Assay

Incubation samples are prepared by adding a human liver microsomal preparation to the test inhibitor (final concentrations 0.05 mg/mL protein, 10 μM inhibitor in 100 mM $NaPO_4$, pH 7.4 buffer) and mixed. Samples are pre-incubated for approximately five minutes at 37° C. Following the pre-incubation period, the reaction is initiated with the addition of a solution containing NADPH and midazolam, as the enzyme substrate, (final concentration 1 mM NADPH, 5 μM midazolam). After addition of the NADPH solution, the samples are incubated for 3 minutes at approximately 37° C. Following the incubation period, the reaction is quenched by the addition of 50 μL of methanol (and an internal standard for chromatography) and the samples are mixed well. After quenching the reaction, the mixture is centrifuged at approximately 4000 rpm for 15 minutes at approximately 5° C. and analyzed by LC/MS analysis.

Samples are analyzed using HPLC/MS with gradient elution on short conventional C18 columns (Loading Mobile Phase—95/5 Milli-Q® $H_2O$/methanol (v/v) with 1% acetic acid. Mobile Phase B—80/20 Milli-Q® H$_2$O/methanol (v/v) with 1% acetic acid. Mobile Phase C—5/95 Milli-Q® H$_2$O/methanol (v/v) with 1% acetic acid. Rinsing Mobile Phase—75/25 Milli-Q® H$_2$O/acetonitrile (v/v)).

The samples are injected into a Mass Spectral Analyzer for Selected Ion Monitoring (SIM) at a mass of 342.1 (1-OH-midazolam) and 346.1 (α-hydroxymidazolam-d4 internal standard) using TurboIon Spray under positive conditions. Data are reported as % inhibition of the formation of 1-OH-midazolam in the presence of an inhibitor concentration of 10 μM.

Following the protocol described, Example 1a displays 13.5% CYP3A4 inhibition. Compounds, such as Example 1a, that demonstrate low reversible CYP3A4 inhibition potential have a reduced likelihood for negative interactions with other medications that could result in medication dosage changes or a need to stop medication in a patient. Thus, such compounds are desirable and have improved safety profiles.

In Vitro Mechanism-Based Inhibition of CYP3A

The compound of Example 1a is evaluated as a mechanism-based inhibitor of CYP3A with the goal of obtaining kinetic constants of k$_{inact}$ and K$_I$ for this interaction. (K$_{inact}$ is the maximum rate constant of inactive enzyme complex formation. K$_I$ is the concentration at half maximal inactivation). The compound is incubated with human liver microsomes (pool of human liver microsomes with high expression of CYP3A4 activity) in a two stage in vitro incubation: an inactivation reaction, which allows the inhibitor to inactivate the enzyme, and an activity assay, which assesses the remaining activity of the microsomal protein using 1'-hydroxylation of midazolam as the probe.

Inactivation reactions (100 μL final volume) containing 100 mM sodium phosphate buffer (pH 7.4), 1 mM EDTA (ethylenediaminetetracetic acid), in the absence or presence of 1 mM NADPH (nicotinamide adenine dinucleotide phosphate, reduced), with concentrations ranging from 0.75 μM-24 μM of test compound are preincubated for 3 minutes at 37° C. in triplicate. Inactivation reactions are initiated with the addition of the high CYP3A activity microsomal pool (CellzDirect, Austin Tex., 0.5 mg/mL). At multiple time points (0, 2.5, 5, 10, and 30 minutes), 5 μL aliquots of the inactivation reaction mixtures are withdrawn and diluted 1/20 into a prewarmed (37° C.) CYP3A4 activity assay incubation system (95 μL) containing 1 mM NADPH and midazolam (100 μM). This activity assay mixture, at 0.025 mg/mL final protein concentration and 1/20 of the inhibitor concentration, is incubated (37° C.) for an additional one minute prior to stopping the reaction with the addition of 50 μL of MeOH. Samples are mixed and denatured protein is removed by centrifugation at 4000 rpm for 10 minutes.

The formation of 1'-OH midazolam is analyzed by LC/MS/MS with a gradient elution on a Phenomenex Synergi 4μ. Hydro-RP column (Mobile Phase A—95/5 Milli-Q® H$_2$O/methanol (v/v) with 5 mM ammonium acetate, Mobile Phase B—5/95 Milli-Q® H$_2$O/methanol (v/v) with 5 mM ammonium acetate, Needle Wash Solvent A—0.4% trifluoroacetic acid in 90/10 acetonitrile/Milli-Q® H$_2$O (v/v), Needle Wash Solvent B—50/50 Milli-Q® H$_2$O/methanol (v/v)). The samples are injected into a Sciex API 4000 for Selected Reaction Monitoring at a mass of 342.0 (1-OH-midazolam) and 347.0 (α-hydroxymidazolam-d3 internal standard) using TurboIon Spray under positive conditions.

The loss of 1'-OH midazolam formation (CYP3A4 activity) in the microsomal incubations is plotted as the log percent remaining CYP3A4 activity as a function of preincubation time for each test compound concentration. Kinetic parameters for inactivation are determined using WinNonlin Professional to fit the following equations to the data:

$$\text{percent inhibition}_{(t)} = 100_{(t=0)} * e^{(-\lambda t)} \qquad \text{Equation 1:}$$

Where λ is defined as $$\lambda = (k_{inact} * I)/(K_I + I) \qquad \text{Equation 2:}$$

The loss of activity for the compound of Example 1a, ranges from 11%-22% and is not concentration dependent. Therefore, values for k$_{inact}$ and K$_I$ from equation 2 cannot be determined. Based on these data, the compound of Example 1a is not a mechanism based inhibitor of CYP3A4. Compounds, such as Example 1a, that demonstrate low or no mechanism-based irreversible CYP3A4 inhibition potential have a reduced likelihood for negative interactions with other medications that could result in medication dosage changes or a need to stop medication in a patient. Thus, such compounds are desirable and have improved safety profiles.

We claim:

1. A method of treating cancer selected from the group consisting of brain cancer, basal cell carcinoma, esophagus cancer, gastric cancer, pancreatic cancer, biliary tract cancer, prostate cancer, breast cancer, small-cell lung cancer, non-small cell lung cancer, B-cell lymphoma, multiple myeloma, ovarian cancer, colorectal cancer, liver cancer, kidney cancer, melanoma, head and neck cancer, soft tissue sarcomas, bone sarcomas, and leukemia in a mammal comprising administering to the mammal an effective amount of a compound which is 4-fluoro-N-methyl-N-(1-(4-(1-methyl-1H-pyrazol-5-yl)phthalazin-1-yl)piperidin-4-yl)-2-(trifluoromethyl)benzamide, or a pharmaceutically acceptable salt thereof.

2. The method according to claim 1 wherein the cancer is basal cell carcinoma.

3. The method according to claim 1 wherein the cancer is pancreatic cancer.

4. The method according to claim 1 wherein the cancer is brain cancer.

5. The method according to claim 4 wherein the brain cancer is medulloblastoma.

6. The method according to claim 1 wherein the cancer is small-cell lung cancer.

* * * * *